(12) United States Patent
Stahl

(10) Patent No.: US 6,950,755 B2
(45) Date of Patent: Sep. 27, 2005

(54) GENOTYPE PATTERN RECOGNITION AND CLASSIFICATION

(75) Inventor: Douglas C. Stahl, Claremont, CA (US)

(73) Assignee: City of Hope, Duarte, CA (US)

(*) Notice: Subject to any disclaimer, the term of this patent is extended or adjusted under 35 U.S.C. 154(b) by 320 days.

(21) Appl. No.: 09/895,381

(22) Filed: Jul. 2, 2001

(65) Prior Publication Data

US 2003/0003459 A1 Jan. 2, 2003

(51) Int. Cl.$^7$ ............................ G01N 33/48; G06K 9/00; G06K 9/62; G06K 9/36

(52) U.S. Cl. ........................... 702/19; 382/129; 382/155; 382/280

(58) Field of Search ........................... 702/19; 382/129, 382/155, 280

(56) References Cited

U.S. PATENT DOCUMENTS

| | | | |
|---|---|---|---|
| 5,365,455 A | 11/1994 | Tibbets et al. | 364/497 |
| 5,502,773 A | 3/1996 | Tibbetts et al. | 382/129 |
| 5,541,067 A | 7/1996 | Perlin | 435/6 |
| 5,580,728 A | 12/1996 | Perlin | 435/6 |
| 5,741,648 A | 4/1998 | Hemstreet, III et al. | 435/6 |
| 5,845,049 A | 12/1998 | Wu | 395/22 |
| 5,945,289 A | 8/1999 | Lehrer | 435/6 |
| 5,955,595 A | 9/1999 | Korsmeyer | 536/23.5 |
| 6,054,268 A | 4/2000 | Perlin | 435/6 |
| 6,088,099 A | 7/2000 | Cabib et al. | 356/345 |

OTHER PUBLICATIONS

Ewing et al. (Genome Research (1998) vol. 8, pp. 175–185).*

Youssef (A Lecture Series on Data Compression (translation 1996 by Speilman@NIST.GOV) pp. 1–9).*

Curram et al. (Journal Opl Res. Soc. (1994) vol.45, pp. 440–450.*

Ma et al. (International Journal on Artificial Intelligence Tools (1993) pp. 1–19).*

Allex et al. (Bioinformatics (1999) vol. 15, pp. 723–728).*

M. W. Perlin et al., "Toward Fully Automated Genotyping: Genotyping Microsatellite Markers by Deconvolution," American Journal of Human Genetics, vol. 57, pp. 1199–1210, 1995.

M. Litt et al., "Shadow Bands Seen When Typing Polymorphic Dinucleotide Repeats: Some Causes and Cures," Bio-Techniques, vol. 15, pp. 280–284, 1993.

M. J. Brownstein et al., "Modulation of Non–Templated Nucleotide Addition by Taq Polymerase: Primer Modifications that Facilitate Genotyping," BioTechniques, vol. 20, pp. 1004–1010, 1996.

A. Edwards et al., "DNA Typing and Genetic Mapping with Trimeric and Tetrameric Tandem Repeats," American Journal of Human Genetics, vol. 49, pp. 746–756, 1991.

(Continued)

*Primary Examiner*—Marjorie A. Moran
*Assistant Examiner*—Lori A. Clow
(74) *Attorney, Agent, or Firm*—Fitzpatrick, Cella, Harper & Scinto

(57) ABSTRACT

Interpreting data obtained by analysis of nucleic acids (DNA) by obtaining nucleic acid data in a spatial domain, transforming the nucleic acid data from the spatial domain into a frequency domain, and obtaining sequence data of the nucleic acid data by executing a data mining process on the transformed nucleic acid data. The transformation may be performed by a Hadamard transform, a Fourier transform or a Wavelet transform to obtain frequency coefficients, with less than all of the frequency coefficients being utilized in the data mining process. In addition, the frequency domain data may be normalized prior to the data mining process. The data mining process may be subjecting the frequency coefficients to a connectionist (neural network) algorithm or to a classification tree/rule induction (CART) algorithm.

44 Claims, 10 Drawing Sheets

(1 of 10 Drawing Sheet(s) Filed in Color)

OTHER PUBLICATIONS

A.-K. B. Lindqvist et al., "Chromosome–Specific Panels of Tri–and Tertanucleotide Microsatellite Markers for Multiplex Fluorescent Detection and Automated Genotyping: Evaluation of Their Utility in Pathology and Forensics," Genome Research, vol. 6, pp. 1170–1176, 1996.

T. J. Hudson et al., in "PCR Methods of Genotyping," Current Protocols in Human Genetics, vol. 1, pp. 2.5.1–2.5.23, 1997.

J. S. Ziegle et al., "Application of Automated DNA Sizing Technology for Genotyping Microsatellite Loci," Genomics, vol. 14, pp. 1026–1031, 1992.

D. C. Mansfield et al., "Automation of Genetic Linkage Analysis Using Fluorescent Microsatellite Markers," Genomics, vol. 24, pp. 225–233, 1994.

M. W. Perlin et al., "Toward Fully Automated Genotyping: Allele Assignment, Pedigree Construction, and Recombination Detection in Duchenne Muscular Dystrophy," American Journal of Human Genetics, vol. 55, pp. 777–787, 1994.

U.M. Fayyad et al., "From Data Mining to Knowledge Discovery: An Overview," Advances in Knowledge Discovery and Data Mining, MIT Press, pp. 1–34, 1996.

S. Saha, "Image Compression—From DCT to Wavelets: A Review," Crossroads: The ACM Student Magazine, 2000, pp. 12–21.

R. Rohwer et al., "Neural Networks," Machine Learning, Neural and Statistical Classification, Ellis Horwood, 1994, pp. 84–106.

P. Mars et al., "Artificial Neural Networks," Learning Algorithms: Theory and Application in Signal Processing, Control, and Communications, Electronic Engineering Systems Series, CRC Press, 1996, pp. 25–52.

* cited by examiner

GENOTYPE PATTERN RECOGNITION AND CLASSIFICATION

BACKGROUND OF THE INVENTION

1. Field of the Invention

The present invention concerns automated pattern recognition processes. More particularly, the present invention concerns interpreting data obtained by analysis of nucleic acids by generation of nucleic acid data in a spatial domain, transformation of the data from the spatial domain to a frequency domain, and obtaining sequence data of the nucleic acid data by executing a data mining process on the transformed data.

2. Description of the Related Art

Molecular genetics is one among several disciplines that has accumulated large, complex, information-rich datasets as a result of improved data collection technologies and decreased data storage costs. As a result, a gap between the ability to collect data and the ability to analyze, summarize, classify, and exploit the data for the advancement of biomedical research and patient care is widening rapidly.

In the last decade, major advances in molecular biology have made the need for computer software that can analyze and interpret molecular data rapidly and accurately a necessity. This is primarily due to two major advances in molecular biology that facilitated the rapid development of thousands of genetic markers. First, in 1985, Dr. Kary Mullis discovered that short segments of DNA could be amplified from templates using an enzyme called DNA polymerase and temperature cycling in a process called the polymerase chain reaction (PCR). PCR can amplify over a million duplicate copies of specific DNA sequences in a matter of hours. PCR revolutionized genetic research because it is a fast, inexpensive, and easily automated technique for amplifying minute quantities of DNA for genetic analysis.

Second, in 1989, several laboratories used PCR to demonstrate a high level of polymorphism in a class of tandemly repeated DNA sequences known as microsatellites. The discovery of microsatellites yielded several thousand new highly informative genetic markers and greatly advanced the construction of high-resolution linkage maps.

For a better understanding of how molecular data is obtained for analysis and interpretation, consider the process for human genotyping depicted in FIG. 1. As seen in FIG. 1, a typical genotyping process generally consists of five basic steps: 1) genomic DNA acquisition, 2) multiplexed PCR amplification of microsatellites using flourescently labeled primers, 3) gel electophoresis (allele separation by size), 4) laser-induced fluorescence (allele separation by color), and 5) interpretation of results to determine a genotype.

Acquiring DNA for genotyping can be performed by obtaining DNA primarily from blood, but can also be obtained from bone, hair, and various other fluids, tissues, and cells.

After a sample of DNA is acquired, the different alleles that exist at specific microsatellite marker locations of interest are amplified by PCR in sufficient quantities for subsequent analytical processing. A pair of PCR primers is designed to amplify the alleles at each marker location. The simultaneous amplification of multiple microsatellites using multiple pairs of primers in a single polymerase chain reaction is called multiplexing. This approach allows hundreds of microsatellites to be amplified in a single experiment.

Multiplexing often generates PCR products that overlap in size, making them difficult to separate. However, multiplexed PCR is greatly enhanced by the use of fluorescent labeling technology. By attaching different fluorescent labels to PCR primers, a scanning laser can be used to distinguish the different alleles by different wavelengths, even when their sizes overlap.

Alleles are typically separated by size in a process called gel electrophoresis. The gel electrophoresis process uses an electric current to force molecules through pores in a thin layer of polyacrylamide gel. The gel is made with pores designed for separating molecules in specific size ranges. The electric current causes the alleles to travel across the gel, with smaller alleles traveling farther across the gel than larger alleles. Fluorescent size standards are also included to calibrate and improve the accuracy of allele size determination.

When excited by a laser, the fluorescent labels on the PCR primers emit light at specific wavelengths corresponding to different colors in the visible light spectrum. Automated DNA sequencers typically use a scanning laser to detect the fluorescently-labeled alleles on each polyacrylamide gel. A digital detector records the multicolored fluorescence signals and stores them in machine-readable form. In situations where gel electrophoresis aggregates multiple alleles of similar size, they can be distinguished from one another by their fluorescent labels.

Finally, the electrophoretic patterns must be interpreted to establish a particular genotype. It is this latter portion of the process that has presented difficulty for researchers.

In this regard, the analysis and interpretation of DNA data generally involves various PCR idiosyncrasies that must be analyzed in order to obtain an accurate interpretation of the DNA sequence. When the various PCR problems are combined with each other and with additional sources of background chemical and electrical noise, they result in genotype data that require careful subjective interpretation by an experienced scientist in order to correctly ascertain the true underlying genotypes. However, manual interpretation of genotypes is widely recognized as a fundamental rate-limiting step for high-throughput genotyping and large-scale genome research. While in most cases the analysis and interpretation can be performed with relative ease by experienced human experts, efforts to develop support software for automated genotype interpretation has achieved limited success.

Several approaches have been proposed to simplify the analysis and interpretation of DNA sequences, each of which addresses a subset of the sequencing problems, while other problems are exacerbated or left unresolved. Furthermore, the viability of each approach decreases as the scale of research increases to investigate more complex genetic contributions to disease.

One approach described by M. W. Perlin et al. in "Toward Fully Automated Genotyping: Genotyping Microsatellite Markers by Deconvolution," American Journal of Human Genetics, vol. 57, pp. 1199–1210, 1995, has been the use of microsatellite markers with fewer repeating units. This approach reduces a phenomena known as stutter artifact by sharpening the stutter, but also reduces the polymorphism, informativeness and utility of the markers.

A second approach described by M. Litt et al. in "Shadow Bands Seen When Typing Polymorphic Dinucleotide Repeats: Some Causes and Cures," BioTechniques, vol. 15, pp. 280–284, 1993, and by M. J. Brownstein et al. in "Modulation of Non-Templated Nucleotide Addition by Taq Polymerase: Primer Modifications that Facilitate Genotyping," BioTechniques, vol. 20, pp. 1004–1010, 1996, has been marker-specific modification/customization of PCR conditions to remove signal artifacts. This approach works to a point, but generally does not completely remove artifacts that are intrinsic to the PCR amplification of repetitive units. Additionally, differences in allele size, enzyme concentration, and other experimental factors can have a significant impact on the results. Further, the application of marker-specific PCR conditions is time and labor intensive and generally, a single set of PCR conditions is desirable for consistency and high throughput.

A third approach described by A. Edwards et al. in "DNA Typing and Genetic Mapping with Trimeric and Tetrameric Tandem Repeats," American Journal of Human Genetics, vol. 49, pp. 746–756, 1991, by A.-K. B. Lindqvist et al. in "Chromosome-Specific Panels of Tri- and Tertanucleotide Microsatellite Markers for Multiplex Fluorescent Detection and Automated Genotyping: Evaluation of Their Utility in Pathology and Forensics," Genome Research, vol. 6, pp. 1170–1176, 1996, and by T. J. Hudson et al. in "PCR Methods of Genotyping," Current Protocols in Human Genetics, vol. 1, pp. 2.5.1–2.5.23, 1997, has been substitution of dinucleotide repeat markers with trinucleotide and tetranucleotide repeat markers that are less subject to signal artifacts and easier to interpret. While this approach reduces stutter artifact, it also reduces marker informativeness. Moreover, trinucleotide and tetranucleotide markers are much less prevalent in human genome. Additionally, in some cases, the prominent dinucleotide repeat stutter pattern can be used to distinguish alleles from noise peaks. Further, larger repeat sizes consume larger size windows (relative to their polymorphism) on the polyacrylamide gel, thereby reducing throughput by reducing the ability to multiplex markers.

A fourth approach described by J. S. Ziegle et al. in "Application of Automated DNA Sizing Technology for Genotyping Microsatellite Loci," Genomics, vol. 14, pp. 1026–1031, 1992, and by D. C. Mansfield et al. in "Automation of Genetic Linkage Analysis Using Fluorescent Microsatellite Markers," Genomics, vol. 24, pp. 225–233, 1994, has been analyzing the alleles on the basis of the highest peaks and ignoring the others. This approach succeeds when alleles are widely separated, but fails for closely spaced alleles, complex stutter patterns, and other signal complexities.

Finally, a fifth approach described in U.S. Pat. No. 5,541, 067 to Perlin entitled "Method and System for Genotyping," and by M. W. Perlin et al. in "Toward Fully Automated Genotyping: Allele Assignment, Pedigree Construction, and Recombination Detection in Duchenne Muscular Dystrophy," American Journal of Human Genetics, vol. 55, pp. 777–787, 1994, has been the use of an explicit mathematical model to remove stutter artifact from genotype data by deconvolution. This approach works well for stutter artifact, but does not adequately address other types of signal artifacts and their covariance with stutter artifacts. Additionally, this approach models the stutter artifact as a reproducible response, which is relatively intolerant of noise and the variability of experimental data.

However, as stated above, each of the foregoing idiosyncrasies require careful subjective interpretation and to date, support software for automated genotype interpretation has achieved limited success. Although it is now possible for a single technician to generate data for tens of thousands of genotypes per week, the requisite visual inspection and manual interpretation of genotype data is expensive, tedious, time-consuming, and prone to error. Furthermore, the analyses must be performed by skilled experts that are not abundant in the current workforce. Therefore, a significant obstacle to fully automated genotyping is the analysis and interpretation of data.

SUMMARY OF THE INVENTION

The present invention addresses the foregoing by providing a technique for interpreting complex pattern data (such as nucleic acid data) in which the pattern data is first obtained in a machine-readable form in a spatial domain, is transformed from the spatial domain into a frequency domain, and the transformed data is subjected to a data mining process so as to obtain sequence data.

As a result, the frequency transformation reduces the dimensionality of the pattern data. That is, the frequency transformation removes minor "noise" components from the pattern data while at the same time maintaining major "signal" components. The dimensionality reduction improves classification performance by removing redundancies that otherwise confound the recognition process and conceal the underlying structure of the complex pattern data. In addition, the volume of the spatial domain data, which has conventionally been utilized in the data mining process, is reduced by the frequency transformation. Therefore, less data is subjected to the data mining process, thereby increasing the speed of the process. However, while the volume of data is reduced by the frequency transformation, important characteristics needed to classify the data are maintained. Therefore, the invention also somewhat reduces the processing time over conventional methods while maintaining the classification accuracy.

Thus, in one aspect the invention interprets data obtained by analysis of nucleic acids by obtaining nucleic acid data in a spatial domain, transforming the nucleic acid data from the spatial domain to a frequency domain, and obtaining sequence data of the nucleic acid data by executing a data mining process on the transformed nucleic acid data. The spatial domain data may be obtained by performing gel electrophoresis on nucleic acid material to form an image and transforming the image into a machine-readable format in the spatial domain. The spatial domain may be described in terms of size versus intensity and may be subjected to a normalization process prior to the transformation.

Representative transformation that may be utilized to transfer from the spatial domain to the frequency domain include Hadamard transformation, Fourier transformation, and Wavelet transformation. Each of the foregoing transformations result in frequency coefficients that are then subjected to the data mining process. Preferably, less than all of the frequency coefficients are subjected to the data mining process.

Representative data mining processes may include processing the transformed data in a connectionist neural network algorithm, processing the transformed data in a feedforward, backpropagation connectionist algorithm, and processing the transformed data in a classification tree/rule induction (CART) algorithm. In addition, the CART algorithm may be utilized in conjunction with the Hadamard, Fourier or Wavelet transforms to provide further enhanced results.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

The file of this patent contains at least one drawing executed in color. Copies of this patent with color drawings (s) will be provided by the Office upon request and payment of the necessary fees.

DETAILED DESCRIPTION OF THE PREFERRED EMBODIMENTS

One field of endeavor in which the present invention may be employed is in the field of human genotyping. However, as will be described below, the invention is not limited to human genotyping and may be employed in other fields involving the analysis of nucleic acids or molecular data where the analysis and interpretation of complex patterns are performed. Nonetheless, the following description will be limited to a human genotyping example for the sake of brevity. It should be noted that the following description of a human genotyping process has been provided in a dissertation authored by the inventor herein entitled, "An Application of Knowledge Discovery to Pattern Recognition in Molecular Genetics," presented to the faculty of Claremont Graduate University, Claremont Calif., the contents of which are incorporated by reference as if set forth in full herein.

Figure 1:
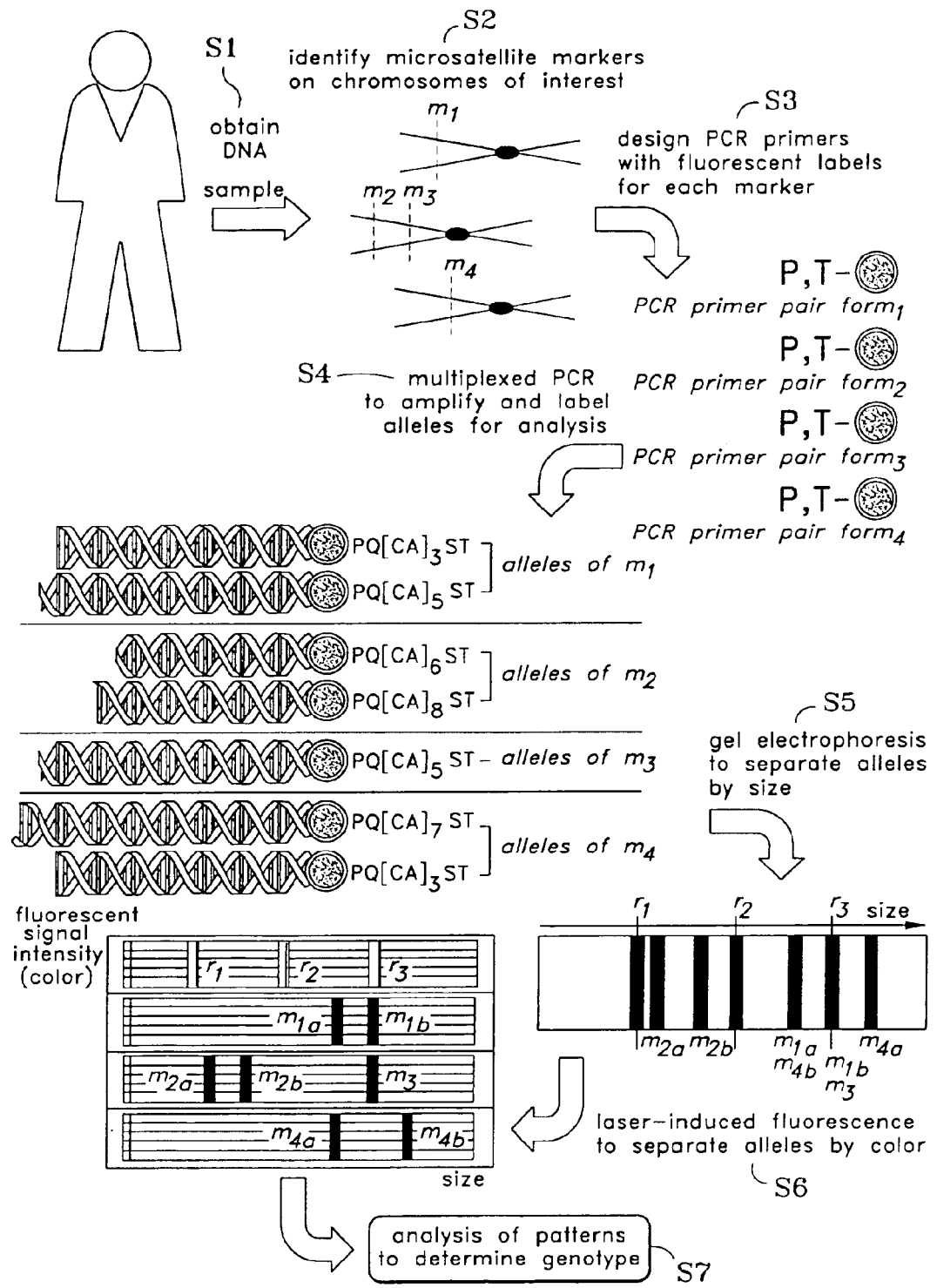
FIG. 1 depicts a typical human genotyping process.
Figure 2:
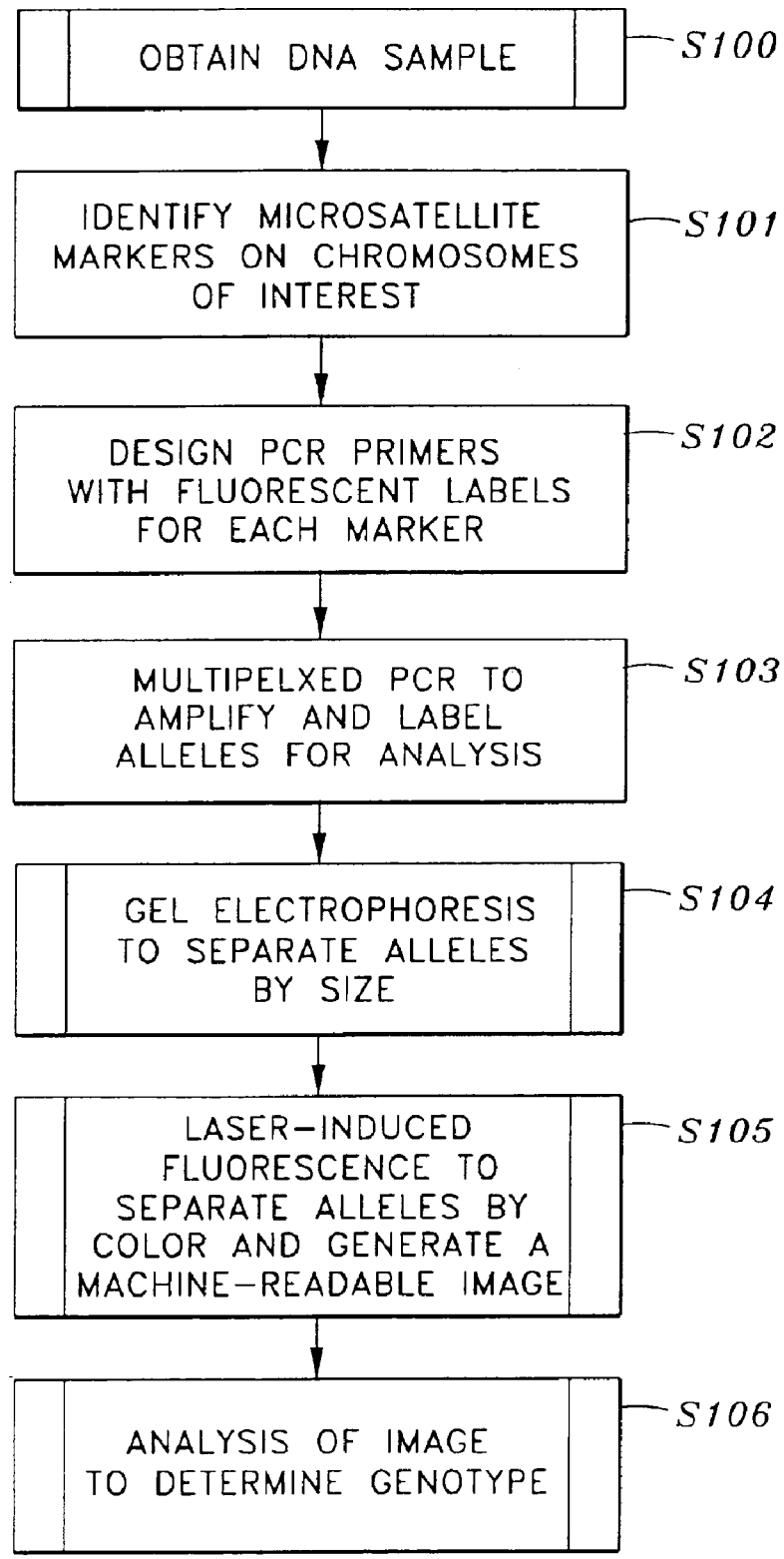
FIG. 2 is a flowchart depicting process steps for a human genotyping process.

FIG. 2 is a flowchart depicting process steps for a human genotyping operation. To briefly summarize the process, a DNA sample is obtained from a human being (step S1), portions of the DNA are amplified by PCR (polymerase chain reaction) processing (steps S2, S3 and S4) and are then subjected to gel electrophoresis (steps S5 and S6) to separate alleles by size and color, an image of the separated alleles is obtained in machine-readable form, and the machine-readable image is then analyzed and interpreted to determine an individual's genotype (step S7).

It should be noted that while the following description focuses on DNA, the invention is not limited to use with DNA but can be utilized with data obtained by the analysis of virtually any "nucleic acid", which can be readily understood to encompass at least DNA, RNA, tRNA, mRNA and rRNA.

A more detailed description of each of the process steps depicted in FIG. 2 will now be provided. Those skilled in the art will readily recognize that at least some of the process steps depicted in FIG. 2 are generally known. That is, the process steps for obtaining DNA from a human, performing PCR and obtaining an image of separated alleles is known and therefore, only a brief description of these processes will be provided below. In addition, various known genotyping methods are available to analyze and interpret the image data to obtain an individual's genotype. However, various problems are inherent in such conventional methods and the present invention address these problems. Therefore, a more detailed description of the analysis and interpretation processes will be provided below.

Returning to FIG. 2, in step S100, an individual's DNA is obtained by extraction from blood, tissue or cells of the individual. Any one of various standard methods for extracting DNA from blood, tissue or cells may be utilized. For instance, DNA may be extracted from anticoagulated human blood removed from the human body by standard venipuncture procedures. Accordingly, any method for extracting DNA can be utilized as long as the DNA is of sufficient purity and quantity to serve as templates for PCR reactions.

PCR is performed in steps S101 to S103. Typically, PCR amplifies alleles that exist at specific microsatellite marker locations of interest (step S101). That is, polymorphic genetic markers within a genome are selected for determining a genotype. Then, in step S102, a pair of PCR primers is designed to amplify the alleles of each marker. The primers may be derivatized with a flourescent detection molecule for immunochemical detection. That is, flourescent labels are added to the PCR primers for each marker to as to uniquely identify each marker location. In step S103, simultaneous amplification of multiple microsatellites using multiple pairs of primers in a single polymerase chain reaction (commonly known as multiplexing) is performed to allow multiple (possibly hundreds) of microsatellites to be amplified in a single PCR experiment. The foregoing is a general description of a well-known PCR process. In practicing the invention, no special PCR process is needed and any amplification process can be utilized.

After PCR processing, gel electrophoresis is performed to separate the labeled PCR products by size (step S104). The separation process is typically performed on a polyacrylamide gel by using an electric current to force molecules through pores in a thin layer of polyacrylamide. The polyacrylamide gel is made with pores designed for separating molecules in specific size ranges. When the electric current is applied to the gel, the alleles travel through the gel with the smaller alleles traveling farther through the gel than the larger alleles. Gel electrophoresis is also a generally known process and in practicing the invention, a typical gel electrophoresis process can be utilized to separate the alleles by size.

Figure 4A:
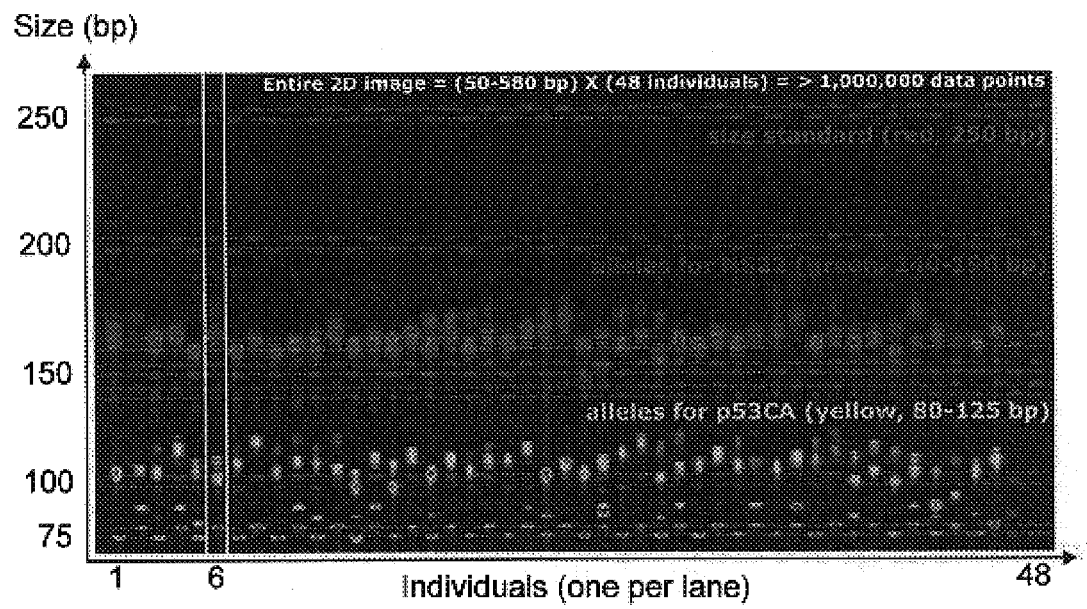
FIG. 4A depicts an image of allele patterns for 48 individuals after gel electrophoresis.

Having separated the alleles by size utilizing gel electrophoresis for example, a standard DNA sequencer can be utilized to generate a machine-readable image of the separated allele pattern (step S105). A typical process consists of using a laser to scan across the gel containing the separated alleles and transforming the scanned data into a machine-readable form. When the laser scans across the gel, it excites the flourescent labels on the PCR primers and when different flourescent labels are used, they emit light at specific wavelengths corresponding to different colors in the visible light spectrum. Therefore, each allele type shows up as a different color when the laser scans the gel. For instance, FIG. 4A depicts an example of a scanned image of the separated alleles in the gel after the alleles have been excited by a laser. FIG. 4A shows two different types of alleles for 48 individuals (each having its own lane as seen in a vertical direction) with the separation of the alleles by size being depicted in terms of base pairs (bp). In the example shown in FIG. 4A, the fluorescent label for one allele type (p53CA) shows up as yellow in the scanned image, while a second allele type (NS22) having a different fluorescent label shows up in the scanned image as green. Thus, in practicing the invention, any process can be utilized to obtain a scanned image depicting different allele types which are separated by size and color, including the process utilized with conventional DNA sequencers. It should be noted that while FIG. 4A depicts an image having 48 lanes corresponding to 48 different individuals, when genotyping one particular individual, one of the lanes is selected for analysis, such as lane 6 which has been separated out and rotated 90 degrees clockwise as shown in FIG. 4B.

Figure 4B:
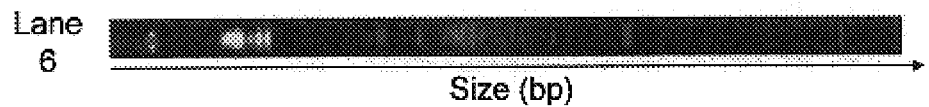
FIG. 4B depicts one lane of the image of FIG. 4B for one of the 48 individuals.

The scanned image, such as that shown in FIG. 4B, is then converted into machine-readable form. This process can be performed by a standard DNA sequencer and is typically done by scanning the gel with a laser to detect the fluorescently-labeled alleles and generating a digital image by a digital detector recording the multicolored fluorescence intensity signals emitted by the alleles. The fluorescence intensity signals are converted into digital (machine-readable) form and stored in a memory medium. This process can also be performed utilizing a typical DNA sequencer.

Figure 5A:
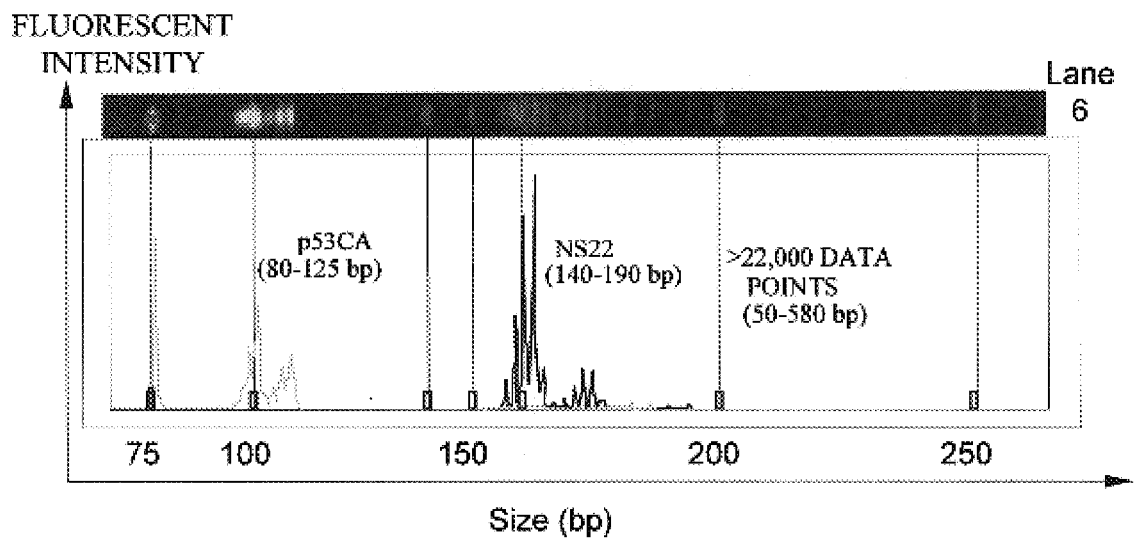
FIG. 5A depicts a graph showing a conversion of the lane of FIG. 4B into a machine-readable form.
Figure 5B:
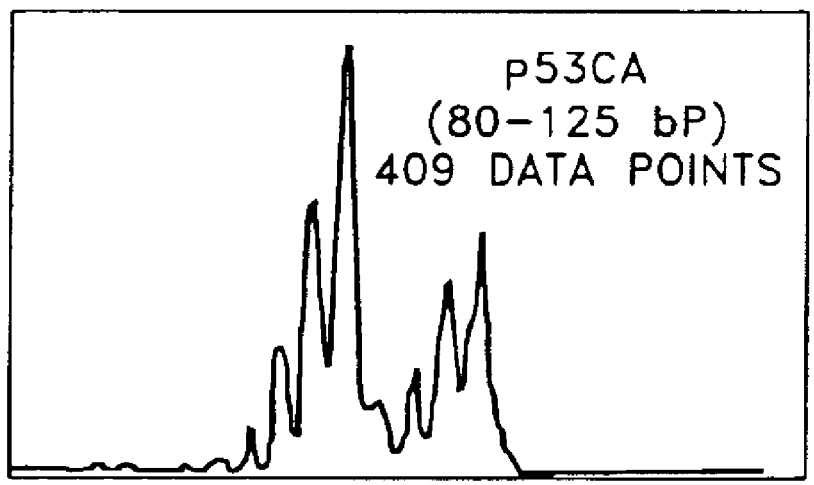
FIGS. 5B and 5C are expanded views of portions of the graph of FIG. 5A.
Figure 5C:
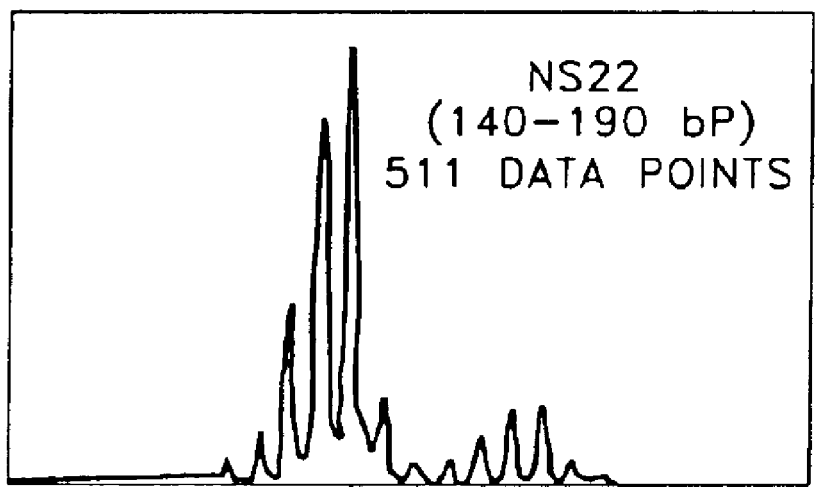

As an example of converting the scanned image into machine-readable form, consider FIGS. 5A to 5C. In this example, lane 6 shown in FIG. 4B is converted into machine-readable form. As seen in FIG. 5A, the laser induced fluorescent intensity data of lane 6 (seen in FIG. 4B) is recorded by a digital detector and converted into machine-readable form to produce the pattern seen in the figure. The machine-readable image is commonly recorded in a spatial domain (i.e. a two-dimensional coordinate system), which is typical for conventional DNA sequencers. For instance, the image may be recorded in terms of allele size versus intensity such as that shown in FIG. 5A. FIG. 5A depicts a pattern of allele size versus fluorescent intensity level for two different allele types (p53CA and NS22). Each of the patterns of FIG. 5A can be segregated by allele type and the pattern of each allele type can be expanded as shown in FIGS. 5B and 5C. The patterns of FIGS. 5A to 5C are recorded and stored in machine-readable form, typically in a spatial domain. The foregoing conversion process of the scanned image into machine-readable form is generally known in the art and any conventional process can be utilized in practicing the invention. However, unlike conventional methods, as will be described below, the machine-readable image is subjected to a transformation process for dimensionality reduction. The transformed data is then subjected to a data mining process for interpretation to obtain an individual's genotype.

It should be noted that while the foregoing description focuses on obtaining a machine-readable image (i.e. an image of complex pattern data) of a DNA sequence for use in human genotyping, the present invention is not limited to human genotyping or even to analysis of nucleic acid data and could be employed with various other applications in which complex pattern data is analyzed and interpreted. For instance, the present invention could be utilized with data obtained from nucleic acids in a Southern/Northern blot analysis or from data obtained from Proteins in a Western blot analysis. Each process generally comprises separating DNA/RNA (Southern/Northern blot) or Proteins (Western blot) via gel electrophoresis, with the separated material being transferred to nitrocellulose paper and the nitrocellulose paper being exposed to a radiolabelled probe. Southern blot analysis is useful for measuring the frequency of genetic patterns. In addition, Northern/Western blot analysis may be used to measure the increased frequency of expression of a particular RNA/Protein, for example, to compare whether a cancerous cell has a higher or lower expression level of a particular RNA/Protein.

Another application in which the invention may be applicable is in the analysis of Protein data that may be obtained in a 2-D gel electrophoresis process in which proteins are separated into two dimensions. In this process, the proteins are first separated by charge, transferred to a second gel, and then separated by size. This technique also has applicability in measuring differences in protein expression in different cells, for example, to assess whether a cancerous cell has altered expression levels of a particular protein. One difference between this technique and Western blot analysis is that all expressed proteins of a cell can be analyzed, as opposed to analysis of particular proteins for which specific probes have been generated.

Other applications in which the invention may be employed may include the analysis of molecular data, such as nucleic acid data or Protein data, obtained by various processes such as chromatography, x-ray diffraction, NMR spectroscopy, and IR spectroscopy. In other words, the invention can be utilized to interpret molecular data, or virtually any complex pattern data, which may be obtained by any process which produces complex pattern data that can be converted into a machine-readable form.

Returning to FIG. 2, having obtained the machine-readable image, the image is analyzed and interpreted to obtain the individual's genotype (step S106). This latter step will now be described in more detail with respect to FIGS. 3A and 3B.

Conventionally, DNA sequencers analyze the machine-readable image obtained in a spatial domain to perform pattern recognition and classification in order to obtain an individual's genotype. This is generally performed by subjecting the raw spatial domain data to a data mining process to perform pattern recognition. For instance, a process has been proposed which performs the following steps: a) create a target data set, b) perform data cleansing and preprocessing, c) perform data reduction and projection, d) select a data mining task, e) select a data mining algorithm, f) perform data mining, g) interpret the mined patterns, and h) consolidate and present the discovered knowledge. (See U. M. Fayyad et al., "From Data Mining to Knowledge Discovery: An Overview," Advances in Knowledge Discovery and Data Mining, MIT Press, pp. 1–34, 1996). However, in the foregoing process, the raw image data is utilized which generally includes minor "noise" components as well as major "signal" components. The noise components generally confound the pattern recognition process and conceal the underlying structure of the complex pattern. As such, the noise components introduce inaccuracies in the pattern recognition process. Also, the raw spatial domain data is somewhat voluminous, thereby adding processing time to an automated pattern recognition process. Unlike conventional methods, the present invention reduces the foregoing inaccuracies by removing the noise components while at the same time retaining the major signal components by performing a dimensionality reduction process on the raw image data. The dimensionality reduction process will be described in more detail below.

Figure 3A:
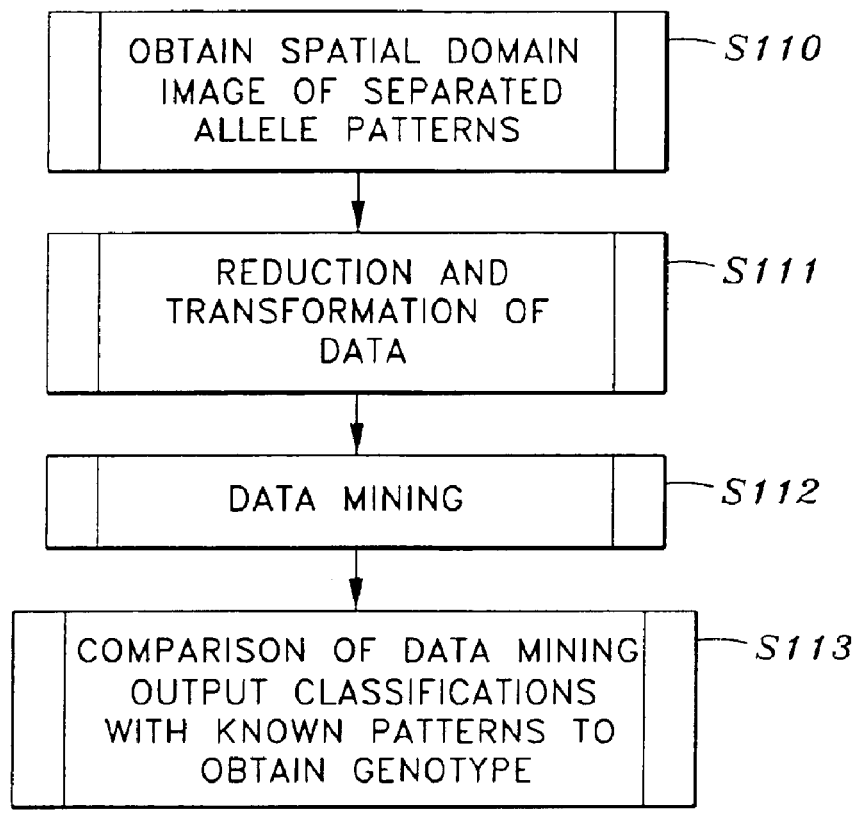
FIG. 3A is a flowchart depicting process steps for an analysis of an image to determine genotype.

Referring now to FIG. 3A, process steps are depicted for analyzing and interpreting the machine-readable image according to the invention. In step S110, the machine-readable image obtained in a spatial domain is recorded as described above. Unlike conventional methods, in the invention, the machine-readable spatial domain data is first subjected to transformation and data reduction processes (step S111) before being subjected to a data mining process. These processes are depicted in more detail in FIG. 3B.

Figure 3B:
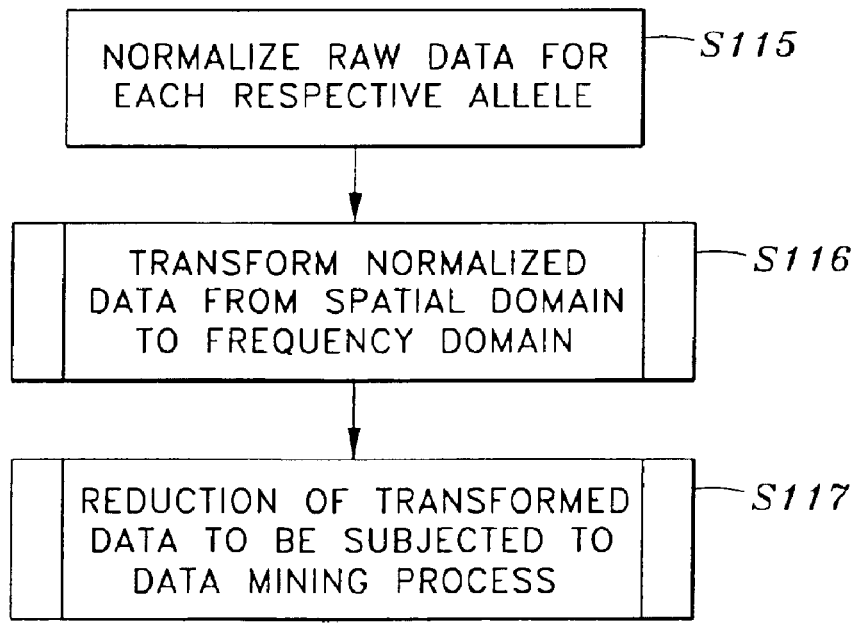
FIG. 3B is a flowchart depicting process steps of a data transformation and reduction process.
Figure 6A:
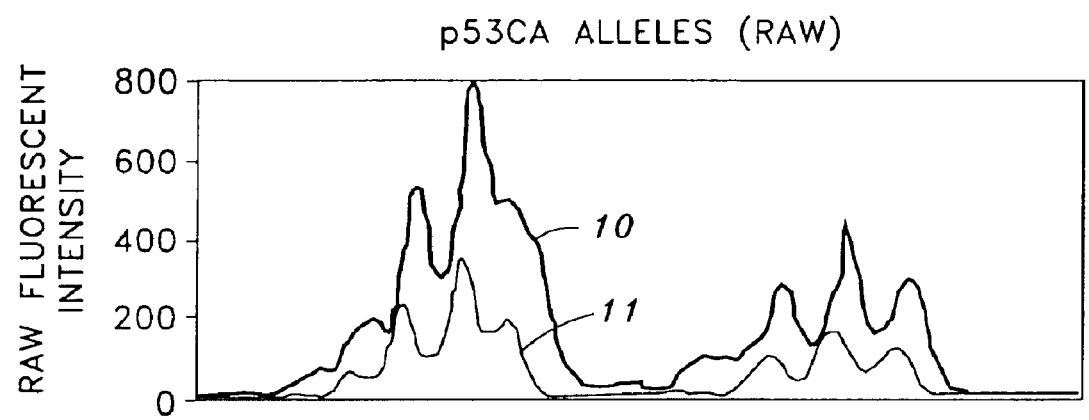
FIG. 6A is a graph depicting raw fluorescent intensity values for one allele type of two different individuals.
Figure 6B:
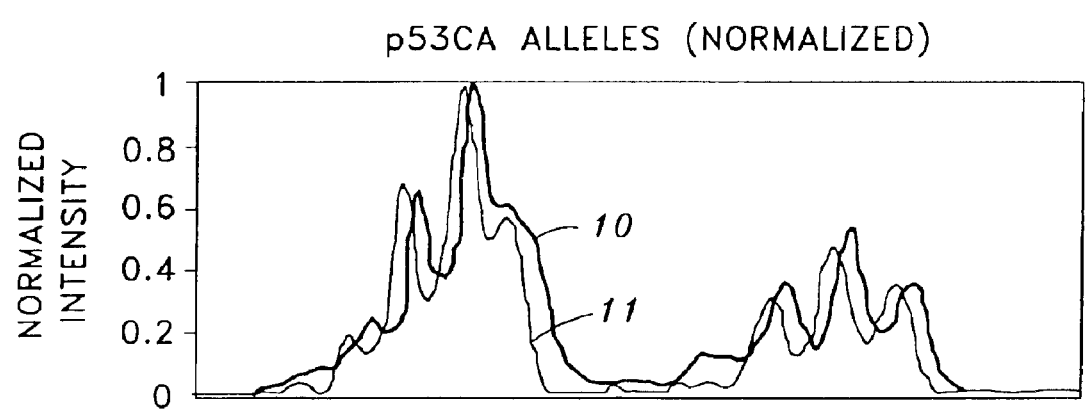
FIG. 6B is a graph of the data of FIG. 6A after a normalization process.

As seen in FIG. 3B, in step S115 raw spatial domain data obtained from the machine-readable image is subjected to a normalization process. Due to the different colored fluorescent labels, large differences in absolute fluorescent signal intensity values result when the scanned image is converted into digital form. Normalization is therefore utilized as a process to compensate for the absolute fluorescent signal intensity value differences and to reduce intrinsic dimensionality of the raw data while preserving the features necessary for allele classification. The normalization process preferably comprises dividing the raw fluorescent intensity values of each allele type by the maximum fluorescent intensity value of each allele type. An example of the resultant data after a normalization process is depicted in FIGS. 6A and 6B, where the raw data for one allele (p53CA) of two different individuals (reference numbers 10 and 11) is depicted in FIG. 6A and the resulting normalized data for the same two alleles of the same two individuals being depicted in FIG. 6B.

Returning to FIG. 3B, after the normalization process of step S115, the normalized spatial domain data is then subjected to transformation and data reduction processes (steps S116 and S117). That is, the normalized spatial domain data obtained in steps S110 and S115 is preferably transformed from the spatial domain to a frequency domain to obtain frequency coefficients corresponding to the spatial domain values. One object of the transformation process is to minimize "within-class" variability and the maximize "between-class" variability of features of interest, such as allele patterns for example. Additionally, the transformation process serves to reduce the number of variables to be considered in the data mining process. Moreover, transforming the spatial domain data into the frequency domain removes or recodes redundancies that often confound conventional pattern recognition processes and conceal underlying structures of complex patterns.

The transformation is preferably performed utilizing a Hadamard transform, however other transforms could be utilized, including Fourier transforms and Wavelet transforms. In this regard, both Hadamard and Fourier transforms are analogous in that both algorithms decompose functions into a series of frequency components. Although both possess similar data reduction capabilities, the Hadamard transform provides some advantages in that it yields the same basic data reduction benefits as the Fourier transform, but uses 50% fewer coefficients. Therefore, the Hadamard algorithm is less than half the size of its Fourier counterpart and is three to eight times faster when applied to the same waveform on equivalent computer hardware.

Another type of transform that may be utilized in place of either a Hadamard or a Fourier transform is a Wavelet transform. Such a transform is known and has been described in detail by S. Saha in "Image Compression—From DCT to Wavelets: A Review," Crossroads: The ACM Student Magazine, 2000, pp. 12–21. Use of a Wavelet transform may further reduce the dimensionality and result in faster and more accurate processing. Regardless of the type of transform chosen, the invention is not limited to any one in particular and any type of transform can be employed in practicing the invention. Preferably, however, the transform results in frequency coefficients that are thereafter used in the following data mining step.

In the present embodiment, the output of the frequency transformation results in frequency coefficients that are equal to the spatial domain values input in the transform. However, the data can be reduced due to ordering of the frequency coefficients induced by the transformation, such that less than all of the frequency coefficients are used in the data mining. Prior to the transformation process, the frequency characteristics are distributed throughout each pattern. However, after the transformation, the frequency coefficients are ordered so that the first few contain information about the rough contours of the original pattern, while the remainder describe the details of the pattern. As such, the data can be reduced by considering only the coefficients that provide the rough contour information, provided that they are sufficient to maintain the necessary features needed for classification.

Referring again to FIG. 3B, after the spatial domain image data is transformed to the frequency domain, a data reduction process is employed to reduce the amount of frequency domain data to be subjected to the data mining process (step S117). Any method of reducing the data can be employed, including ignoring certain of the data values or setting a certain number of the data values to be equal to zero. However, the data reduction process should maintain the features of the features of interest (allele patterns) and therefore, the type of data reduction process utilized should be selected accordingly. As stated above, the transformation process results in frequency coefficients that are ordered such that the first few contain rough contour information of the features of interest (allele pattern) while the remaining coefficients contain the details. Therefore, if the first few coefficients contain sufficient information to maintain the pattern contour within a specified range to allow effective pattern recognition, the remainder of the coefficients would be mere surplusage and could be discarded. As will be described below, it has been found that this is an effective method for reducing the frequency data and in particular, that the amount of the frequency data which results from the frequency transformation can be reduced to ⅛ the original amount (after the Hadamard transformation process) while maintaining the contour of the pattern to provide for effective pattern recognition.

Figure 7A:
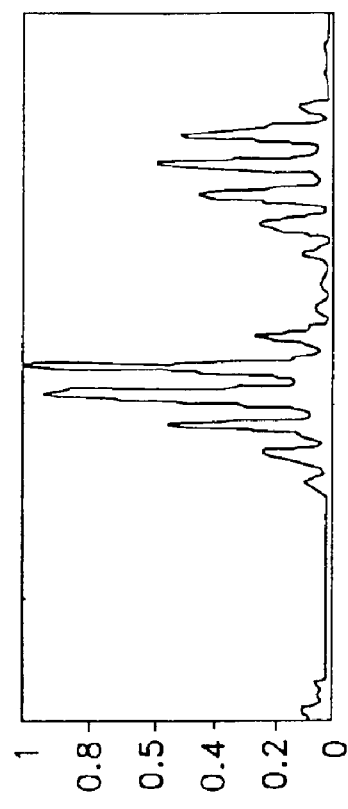
FIGS. 7A and 7B depict normalized intensity data for two different allele types.
Figure 7B:
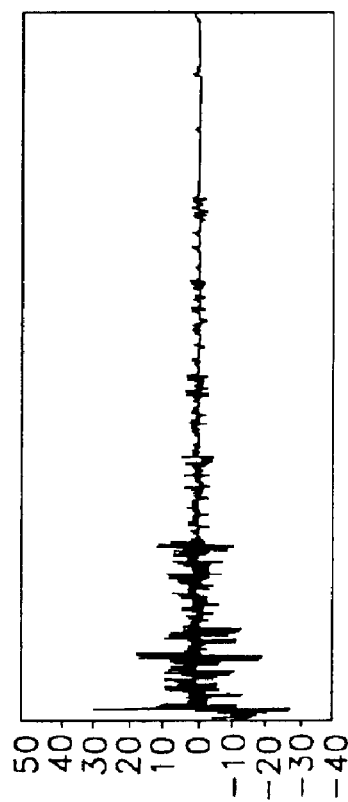
Figure 7C:
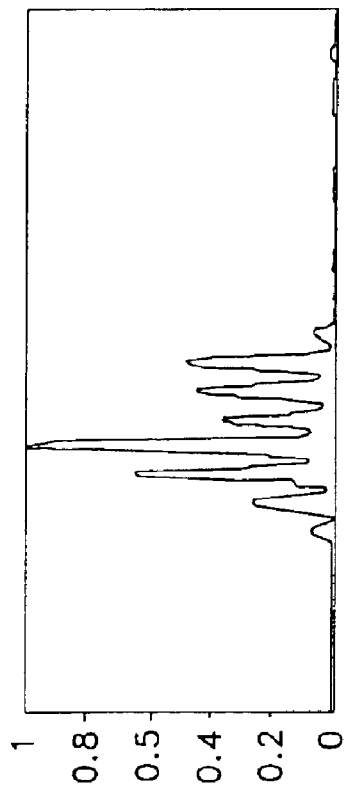
FIGS. 7C and 7D depict a graph of the normalized data of FIGS. 7A and 7B, respectively, after being transformed to a frequency domain.
Figure 7D:
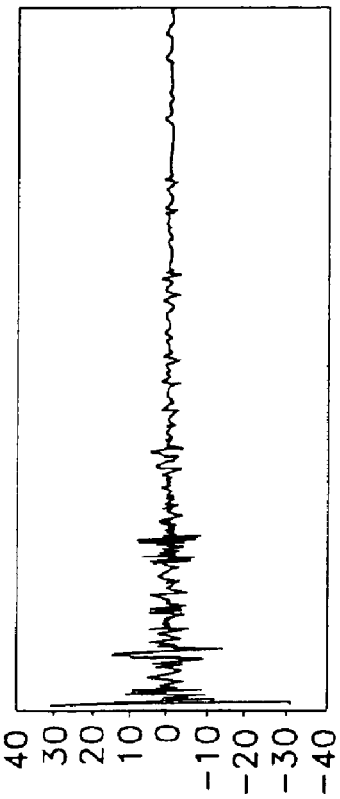
Figure 7E:
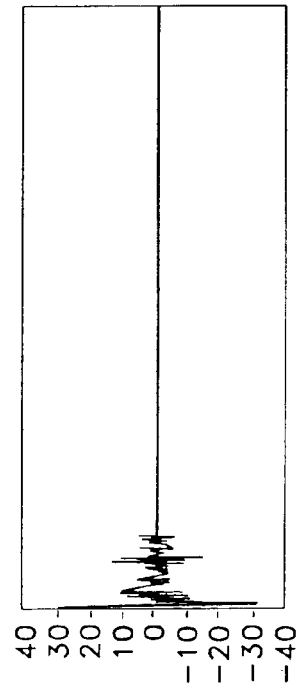
FIGS. 7E and 7F depict the frequency data of FIGS. 7C and 7D, respectively, after a data reduction process.
Figure 7F:
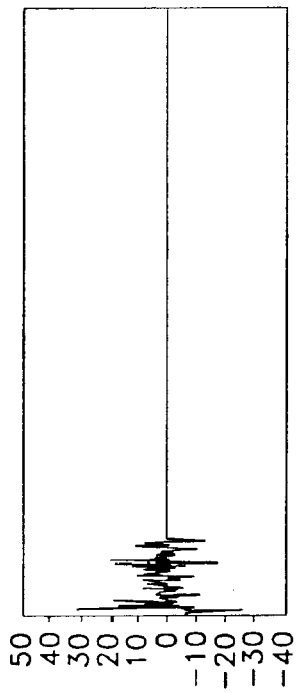

FIGS. 7A to 7J depict an example of a frequency transformation and data reduction process according to the invention for one allele type (NS22) of two different individuals. FIGS. 7A, 7C, 7E, 7G and 7I are for one individual and FIGS. 7B, 7D, 7F, 7H and 7J are for a second individual. FIGS. 7A and 7B depict a plot of normalized spatial domain data for 512 fluorescent intensity values for each of the two individuals. The normalized spatial domain data of FIGS. 7A and 7B is subjected to the Hadamard transformation to obtain 512 frequency coefficients. The 512 frequency coefficients which result from the Hadamard transformation have been plotted as shown in FIGS. 7C and 7D, respectively. The transformed frequency coefficient data of FIGS. 7C and 7D is then subjected to a data reduction process. In the present example, the frequency data is reduced by utilizing only the first few coefficients that define the rough pattern contour while setting the remaining coefficients to zero. In this regard, it has been found in the present example that the first 64 (⅛ of the 512 original input values) coefficients provide the rough contour information needed to perform pattern recognition. Therefore, the data has been reduced by setting all but the first 64 of the 512 coefficients to zero. Of course, it can readily be understood that the number of coefficients that can be set to zero is not limited to the last 448 and any number of coefficients which maintain the essential features of the features of interest (allele patterns) can be utilized. Additionally, the invention is not limited to setting the coefficients to zero and they may simply be ignored instead, or any other data reduction process could be utilized. A plot of the remaining 64 frequency coefficients, where all but the first 64 are set to zero, for each of FIGS. 7C and 7D are depicted in FIGS. 7E and 7F, respectively. Thus, the frequency coefficient data for the 512 data values has been reduced to 64 Hadamard coefficients which are to be subjected to the data mining process. Accordingly, for the present example, a ⅞ reduction in the amount of data can be achieved while still maintaining the essential features of the pattern to perform an effective pattern recognition process.

Figure 7G:
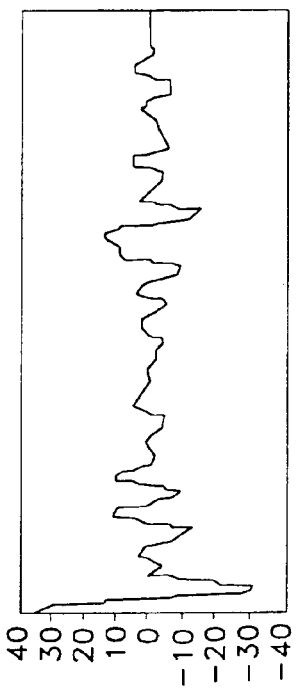
FIGS. 7G and 7H depict the data of FIGS. 7E and 7F, respectively, in expanded format.
Figure 7H:
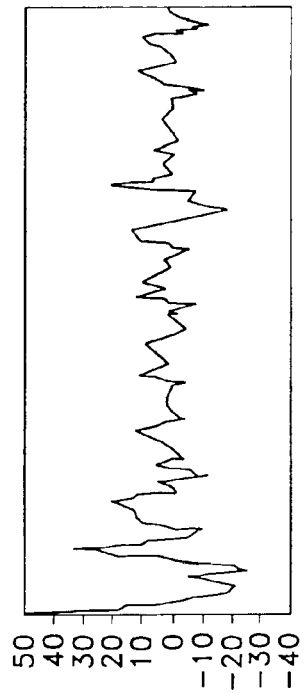
Figure 7I:
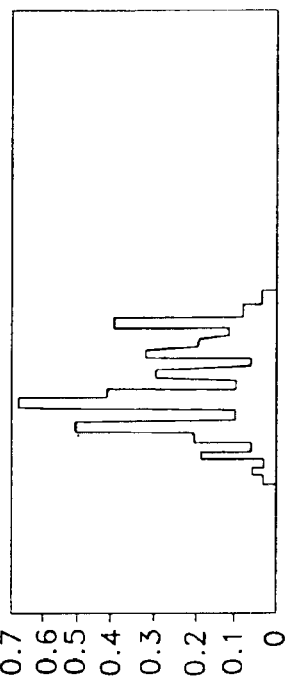
FIGS. 7I and 7J depict the data of FIGS. 7E and 7F, respectively, after being subjected to an inverse transformation from a frequency domain back to a spatial domain.
Figure 7J:
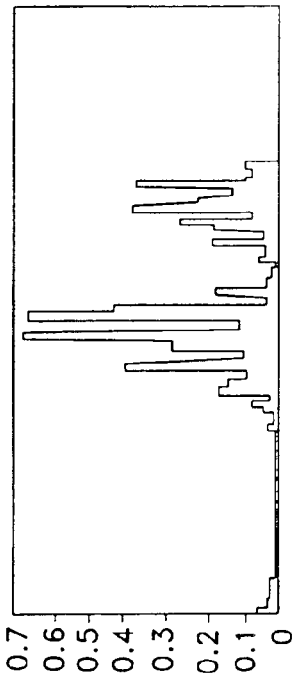

To confirm that the essential features of the pattern contour have been maintained, reference is made to FIGS. 7G to 7J. FIGS. 7G and 7H depict the 64 Hadamard coefficients of FIGS. 7E and 7F in expanded form. When these 64 coefficients are subjected to an inverse Hadamard transform, the plots shown in FIGS. 7I and 7J result. As can readily be seen in FIGS. 7I and 7J, although the plots are slightly distorted and attenuated as compared with the original spatial domain plots of FIGS. 7A and 7B, the essential features of each allele pattern needed for pattern classification has been maintained while at the same time, the amount of data to be subjected to the data mining process has been reduced to ⅛ the original amount.

Having performed transformation and data reduction according to the foregoing, the transformed and reduced data is then subjected to a data mining process (step S112). In the present example, after having obtained the 64 coefficients for each allele type via the transformation process, the 64 coefficients are then subjected to a data mining process for pattern recognition. The data mining process utilized in the present invention is preferably a connectionist (neural network) algorithm. For example, the data mining process may be performed by an artificial neural network such as those described by R. Rohwer et al. in "Neural Networks," Machine Learning, Neural and Statistical Classification, Ellis Horwood, 1994, pp. 84–106, and by P. Mars et al. in "Artificial Neural Networks," Learning Algorithms: Theory and Application in Signal Processing, Control, and Communications, Electronic Engineering Systems Series, CRC Press, 1996, pp. 25–52. Alternatively, the data mining process may be a classification tree/rule induction (CART) algorithm. In this regard, it has been found that use of a CART algorithm in connection with the Hadamard transformation and the Wavelet transformation offer additional efficiency and accuracy advantages over the use of a neural network and therefore, it is preferable that such a combination be utilized. However, the invention is not limited to use of a neural network or a CART algorithm and any type of data mining process used in pattern recognition can be utilized instead.

Moreover, a customized data mining process could also be utilized and the following description provides more detail of one possible customized data mining process.

A data mining process can generally be described in terms of three primary components: model representation, model evaluation, and search. The following discussion describes an allele classification algorithm in terms of these components.

Model representation refers to the language used for describing discoverable patterns. An allele classifier model is essentially a connectionist network that conveys concepts via weighted connections between simple processing elements (PEs). A network architecture can be developed and refined through an iterative process of building and testing different topologies to evaluate their learning capabilities.

Figure 8:
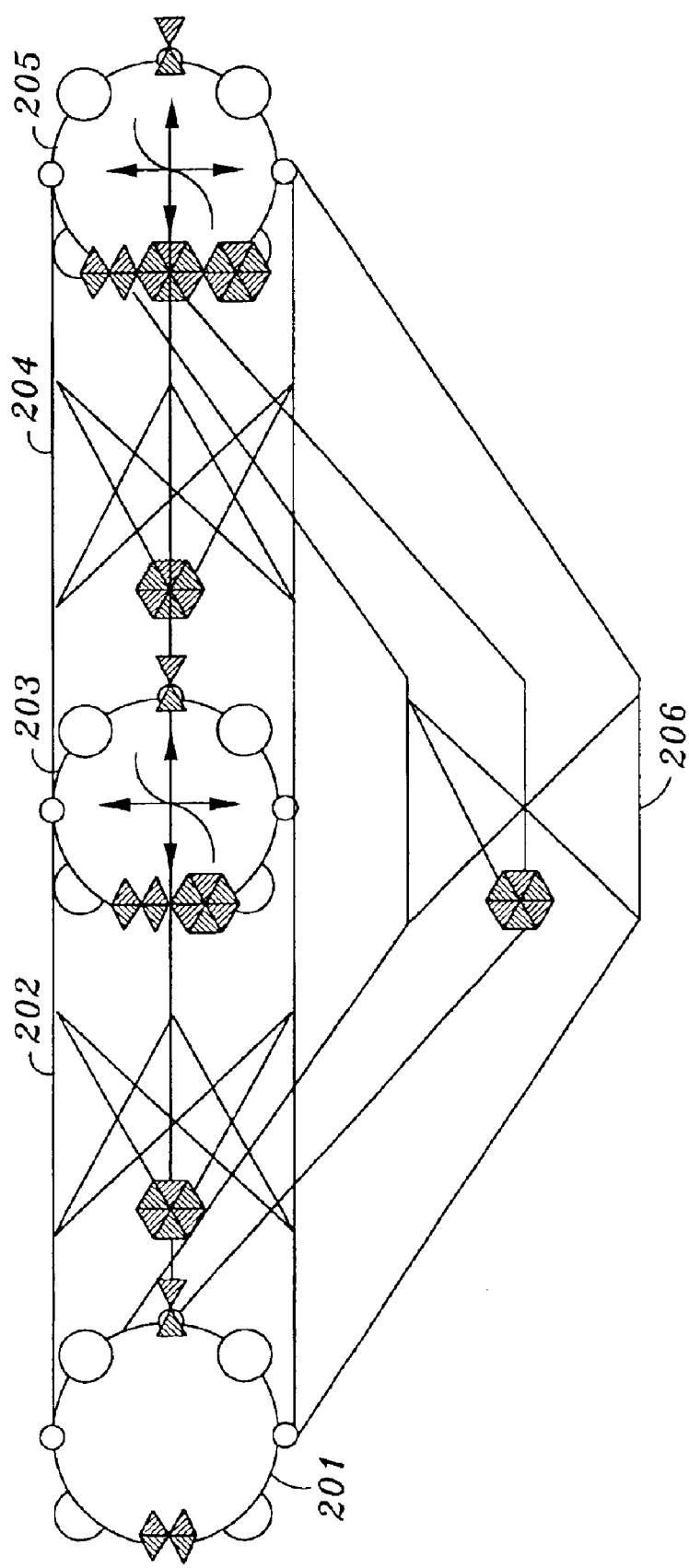
FIG. 8 depicts a representative model of a neural network for performing data mining.

A conceptual diagram of what has been found to be an effective network topology for allele classification is shown in FIG. 8. FIG. 8 depicts processing elements for processing one of the plural input coefficient values (64 coefficients for the example described above with respect to FIGS. 7A to 7J). However, it can be readily understood that a more complete topology would include processing elements for processing all of the plural (64 in the example) input coefficient values. As seen in FIG. 8, the topology for processing each value consists of an input layer 201, an output layer 205, a hidden layer 203 and weighted connections 202 and 204. Each processing element (PE) in the input layer 201 is connected to PEs in the feature extraction or "hidden" layer of the topology, resulting in 1216 weighted connections between the two layers. The number of PEs in the feature extraction layer is selected empirically to optimize classification performance while minimizing the risk of overfitting training data.

Each PE in the feature extraction layer serves to "add up the evidence" presented to it and "make a decision" by applying a nonlinear activation function to the summarized input signals. The nonlinearity serves as a source of internal competition that forces different PEs to specialize in different regions of the input space. A hyperbolic tangent (tanh) nonlinearity may be chosen for allele classification because it is defined continuously over the same interval (−1,1) as the normalized inputs to the classifier. Information presented to each PE in the feature extraction layer is summed and multiplied by a tanh nonlinearity function before being propagated to subsequent layers of the network over a second set of weighted connections 204 to each PE in the output layer 205. The number of PEs in the output layer is defined independently for each genetic marker based on the number of allele categories required for classification.

For instance, in the example described above, exemplars for the NS22 marker may contain alleles in 12 different categories. Therefore, the NS22 classifier would contain 228 weighted connections between its feature extraction layer and the 12 PEs of its output layer. Information presented to the output PEs is also transformed through a tanh nonlinearity before being presented as output classifications.

The classifier also includes an additional set of direct connections 206 between the input and output PEs. These direct connections differ from those previously described in that each of the input PEs is connected to only two of the output PEs. If this were a full interconnection, it would consist of 768 (64×12) connections. In contrast, this sparse connection contains only 128 (64×2) connections distributed evenly across the output PEs.

This extra set of connections is a derivative of the standard multilayer perceptron (MLP) architecture known as the generalized feedforward topology. In theory, an MLP network can solve any problem that a generalized feedforward network can solve. In practice, however, generalized feedforward networks often solve problems much more efficiently and learn hundreds of times faster than standard MLPs containing the same number of processing elements. Nonetheless, it has been found that performance improvements are obtained for allele classification after implementation of this topology enhancement.

The second component of the data mining process is model evaluation. Model evaluation estimates how well a particular model and its parameters meet its required criteria. In the present case, the required criteria is predictive accuracy for allele classification.

Predictive accuracy for allele classification can evaluated via cross-validation. Cross-validation consists of dividing training data into m disjoint subsamples, and classifying each subsample using rules developed from the remaining (m −1) subsamples. The estimated error rate for each genetic marker is defined as the average error rate derived from the m subsamples. This evaluation approach maximizes the use of all exemplars for both training and testing while providing an unbiased estimate of classifier performance.

All exemplars for each genetic marker can be randomly assigned to 10 groups, and an input-output pair of data files can be created for each group. The input files contain frequency coefficients for each exemplar. The output files contain each exemplar's expert (supervised) classification. That is, the output files contain the manual classification provided by a genotyping expert. Each row in the output files describes the presence or absence of an allele in each category. A value of (−0.9) indicates the absence of an allele, and a value of (+0.9) indicates the presence of an allele. The use of ±0.9 instead of ±1.0 for supervised learning is recommended as a way to improve classification performance by avoiding the saturation values of the tanh nonlinearity function.

The third component is the search. The preferred search method consists of gradient descent via backpropagation used to optimize model parameters. Such a method can be performed by Quickprop and it has been found that Quickprop consistently produces superior training results and fewer allele classification errors. Quickprop differs from the standard backpropagation algorithm by using information about the second order derivative of the error surface to avoid local minima and accelerate the learning process.

Overfitting is a well-known concern with connectionist learning systems and is directly associated with poor generalization. When training of a connectionist system commences, the mean square error (MSE) for training and validation data generally decrease asymptotically. However, if training is allowed to proceed based only on the network's continuing ability to improve its performance on training data, the MSE for validation data will increase over time. To prevent this problem, an early stopping approach is preferably used to terminate supervised learning at the point of maximum generalization performance on a cross-validation dataset. This approach is generally considered to be an effective way to prevent overfitting in connectionist systems.

Training and testing the classifier consists of a series of experiments for each genetic marker. In each experiment, a different input file is used for cross-validation, and the remaining input-output file pairs are used for supervised learning. Prior to the commencement of each experiment, the weighted connections between PEs are initialized to random values between −1.0 and +1.0. Each experiment consists of multiple presentations of all training data (epochs) and iterative adjustment of connection weights via backpropagation. Each training epoch is followed by a presentation of the cross-validation data without backpropagation to assess the classifier's emerging capabilities. A flowchart describing a simulation process which can be used to evaluate exemplars for each genetic marker is shown in FIG. 9.

Figure 9:
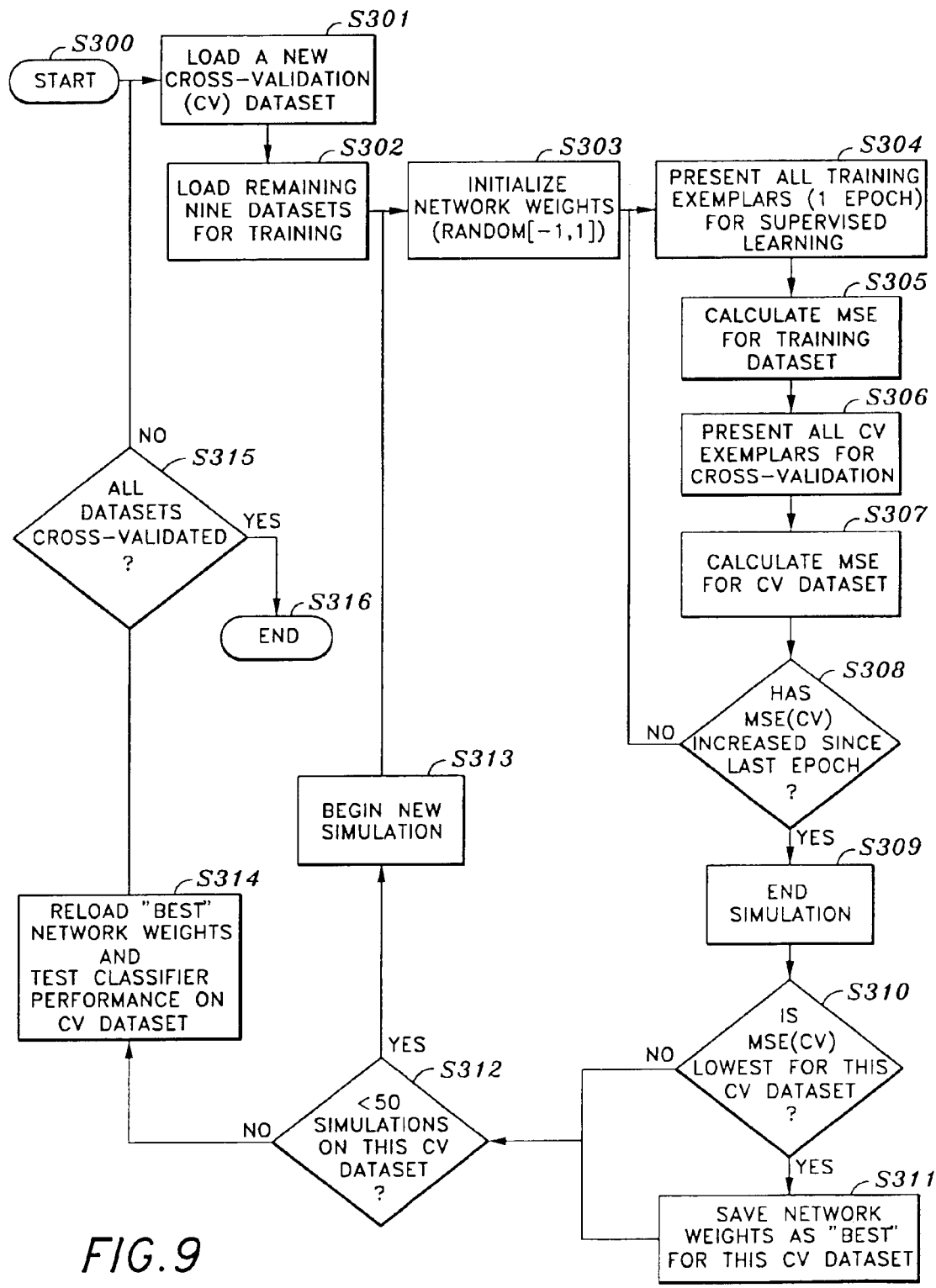
FIG. 9 is a flowchart of process steps depicting a process for training a neural network.

As seen in FIG. 9, in step S301 a new cross-validation (CV) dataset is loaded. Then in step S302, the remaining datasets are loaded for training. Network weights are randomly initialized as either −1 or +1 in step S303 and all training exemplars for supervised learning are presented in step S304. Then in step S305, the MSE for the training dataset is calculated and all cross-validation (CV) exemplars are presented for cross-validation (step S306). The MSE of the cross-validation dataset is calculated in step S307 and in step S308, a determination is made whether the MSE for the CV has increased since the last epoch. If so, then an early termination is performed in step S309. If not, then flow returns to step S304.

After step S309, a determination is made whether the MSE is the lowest for the current CV dataset in step S310. If the determination is YES, then the network weights are saved as "best" for the current CV dataset. If the determination is NO, then a determination is made whether there have been less than 50 simulations for the current CV dataset. If so, then a new simulation is started (step S313) and flow returns to step S303. If not, then the "best" network weights are reloaded and the classifier performance is tested on another CV dataset (step S314). Then, a determination is made in step S315 whether all datasets have been cross-validated and if so, the process ends (step S316). If not, flow returns to step S301.

As can be seen in the foregoing flowchart of FIG. 9, early stopping is used to terminate training at the first sign of an increase in cross-validation MSE. Since connectionist learning is a stochastic process that depends on model parameters and initial conditions, different random values applied to the network connections at the onset of each simulation yields different training results. It is therefore necessary to execute multiple training simulations for each cross-validation data file and save the set of final connection weights that produces the lowest cross-validation MSE. The foregoing process can be accomplished using a macro that executes each simulation 50 times and saves the "best" set of final connection weights for subsequent performance evaluation.

The foregoing simulation process can be performed on a personal computer (PC) workstation. The amount of computer processing time required for each simulation is variable. In situations where the training and cross-validation datasets are very similar, training may proceed for several thousand epochs before an increase in cross-validation MSE is detected. In this case, each simulation may require 10 to 15 minutes for training, and a complete set of 500 simulations may require approximately 100 hours of processing time. In contrast, when the training and cross-validation datasets are dissimilar, training may proceed for only 100–300 epochs before an increase in the cross-validation MSE is detected. In this case, each simulation may last about 1 minute, and a complete set of 500 simulations may require about eight hours of processing time.

Referring again to FIG. 3A, after having performed the data mining process according to the foregoing description, mined patterns output by the data mining process are compared with known patterns to obtain an individual's genotype (step S113). Any conventional process for comparing the mined patterns with known patterns can be utilized and the invention is not limited to any particular method.

As previously stated, the invention is not limited to human genotyping and while the foregoing description was made in the context of human genotyping, the invention can be utilized with other types of pattern recognition processes.

Additionally, it can be readily understood that the foregoing processes can be embodied in a computer program that is executed by computer hardware which includes a processor for executing the computer program. The computer program can be stored on any type of recording medium such as a magnetic drive, floppy disk, tape drive, CD-ROM, flash memory, etc. and the invention is not limited to any particular type of recording medium.

The invention has been described with particular illustrative embodiments. It is to be understood that the invention is not limited to the above-described embodiments and that various changes and modifications may be made by those of ordinary skill in the art without departing from the spirit and scope of the invention.

What is claimed is:

1. A method of identifying and classifying data obtained by the amplification of polymorphic nucleic acids in order to identify alleles, comprising the steps of:
   performing a gel electrophoresis process on polymorphic nucleic acid material and generating a machine-readable image of results of the electrophoresis process, wherein the machine-readable image is in a spatial domain of size versus intensity;
   executing a frequency transform on the spatial domain machine-readable image to transform the spatial domain machine-readable image to a frequency domain, thereby obtaining frequency coefficients corresponding to spatial domain values; and
   executing a pattern-based classification process on the frequency coefficients in order to distinguish alleles from background signals of PCR processing.

2. A method according to claim 1, further comprising performing a normalization process on the spatial domain machine-readable image prior to the transforming step.

3. A method according to claim 1, wherein the transforming step comprises subjecting the spatial domain machine-readable image to a Hadamard transform.

4. A method according to claim 1, wherein the transforming step comprises subjecting the spatial domain machine-readable image to a Fourier transform.

5. A method according to claim 1, wherein the transforming step comprises subjecting the spatial domain machine-readable image to a wavelet transform.

6. A method according to claim 1, further comprising performing a data reduction process on the frequency coefficients so as to reduce the number of frequency coefficients utilized in the classification process.

7. A method according to claim 1, wherein less than all of the frequency coefficients are used in the classification process.

8. A method according to claim 1, wherein the classification process comprises processing the frequency coefficients in a connectionist neural network algorithm.

9. A method according to claim 1, wherein the classification process comprises processing the frequency coefficients in a feedforward, backpropagation connectionist algorithm.

10. A method according to claim 1, wherein the classification process comprises processing the frequency coefficients in a classification tree/rule induction algorithm.

11. A method according to claim 1, wherein the polymorphic nucleic acids comprise one of DNA, RNA, tRNA, mRNA and rRNA.

12. An apparatus for identifying and classifying data obtained by the amplification of polymorphic nucleic acids in order to identify alleles, comprising:
    a memory that stores executable process steps; and
    a processor that executes the executable process steps, wherein the executable process steps comprise (a) generating a machine-readable image in a spatial domain of size versus intensity, the machine-readable image being generated from results of a gel electrophoresis process performed on polymorphic nucleic acid material, (b) executing a frequency transform on the spatial domain machine-readable image to transform the spatial domain machine-readable image to a frequency domain, thereby obtaining frequency coefficients corresponding to spatial domain values, and (c) executing a pattern-based classification process on the frequency coefficients in order to distinguish alleles from background signals of PCR processing.

13. An apparatus according to claim 12, further comprising performing a normalization process on the spatial domain machine-readable image prior to the transforming step.

14. An apparatus according to claim 12, wherein the transforming step comprises subjecting the spatial domain machine-readable image to a Hadamard transform.

15. An apparatus according to claim 12, wherein the transforming step comprises subjecting the spatial domain machine-readable image to a Fourier transform.

16. An apparatus according to claim 12, wherein the transforming step comprises subjecting the spatial domain machine-readable image to a wavelet transform.

17. An apparatus according to claim 12, further comprising performing a data reduction process on the frequency coefficients so as to reduce the number of frequency coefficients utilized in the classification process.

18. An apparatus according to claim 12, wherein less than all of the frequency coefficients are used in the classification process.

19. An apparatus according to claim 12, wherein the classification process comprises processing the frequency coefficients in a connectionist neural network algorithm.

20. An apparatus according to claim 12, wherein the classification process comprises processing the frequency coefficients in a feedforward, backpropagation connectionist algorithm.

21. An apparatus according to claim 12, wherein the classification process comprises processing the frequency coefficients in a classification tree/rule induction algorithm.

22. An apparatus according to claim 12, wherein the polymorphic nucleic acids comprise one of DNA, RNA, tRNA, mRNA and rRNA.

23. Computer-executable process steps for identifying and classifying data obtained by the amplification of polymorphic nucleic acids in order to identify alleles, the executable process steps comprising:
    generating a machine-readable image in a spatial domain of size versus intensity, the machine-readable image being generated from results of a gel electrophoresis process performed on polymorphic nucleic acid material;
    executing a frequency transform on the spatial domain machine-readable image to transform the spatial domain machine-readable image to a frequency domain, thereby obtaining frequency coefficients corresponding to spatial domain values; and executing a pattern-based classification process on the frequency coefficients in order to distinguish alleles from background signals of PCR processing.

24. Computer-executable process steps according to claim 23, further comprising performing a normalization process on the spatial domain machine-readable image prior to the transforming step.

25. Computer-executable process steps according to claim 23, wherein the transforming step comprises subjecting the spatial domain machine-readable image to a Hadamard transform.

26. Computer-executable process steps according to claim 23, wherein the transforming step comprises subjecting the spatial domain machine-readable image to a Fourier transform.

27. Computer-executable process steps according to claim 21, wherein the transforming step comprises subjecting the spatial domain machine-readable image to a wavelet transform.

28. Computer-executable process steps according to claim 23, further comprising performing a data reduction process on the frequency coefficients so as to reduce the number of frequency coefficients utilized in the classification process.

29. Computer-executable process steps according to claim 23, wherein less than all of the frequency coefficients are used in the classification process.

30. Computer-executable process steps according to claim 23, wherein the classification process comprises processing the frequency coefficients in a connectionist neural network algorithm.

31. Computer-executable process steps according to claim 23, wherein the classification process comprises processing the frequency coefficients in a feedforward, backpropagation connectionist algorithm.

32. Computer-executable process steps according to claim 23, wherein the classification process comprises processing the frequency coefficients in a classification tree/rule induction algorithm.

33. Computer-executable process steps according to claim 23, wherein the polymorphic nucleic acids comprise one of DNA, RNA, tRNA, mRNA and rRNA.

34. A computer-readable medium which stores computer-executable process steps for identifying and classifying data obtained by the amplification of polymorphic nucleic acids in order to identify alleles, the computer-executable process steps comprising:

generating a machine-readable image in a spatial domain of size versus intensity, the machine-readable image being generated from results of a gel electrophoresis process performed on polymorphic nucleic acid material;

executing a frequency transform on the spatial domain machine-readable image to transform the spatial domain machine-readable image to a frequency domain, thereby obtaining frequency coefficients corresponding to spatial domain values; and executing a pattern-based classification process on the frequency coefficients in order to distinguish alleles from background signals of PCR processing.

35. A computer-readable medium according to claim 34, further comprising performing a normalization process on the spatial domain machine-readable image prior to the transforming step.

36. A computer-readable medium according to claim 34, wherein the transforming step comprises subjecting the spatial domain machine-readable image to a Hadamard transform.

37. A computer-readable medium according to claim 34, wherein the transforming step comprises subjecting the spatial domain machine-readable image to a Fourier transform.

38. A computer-readable medium according to claim 34, wherein the transforming step comprises subjecting the spatial domain machine-readable image to a wavelet transform.

39. A computer-readable medium according to any claim 34, further comprising performing a data reduction process on the frequency coefficients so as to reduce the number of frequency coefficients utilized in the classification process.

40. A computer-readable medium according to claim 34, wherein less than all of the frequency coefficients are used in the classification process.

41. A computer-readable medium according to claim 34, wherein the classification process comprises processing the frequency coefficients in a connectionist neural network algorithm.

42. A computer-readable medium according to claim 34, wherein the classification process comprises processing the frequency coefficients in a feedforward, backpropagation connectionist algorithm.

43. A computer-readable medium according to claim 34, wherein the classification process comprises processing the frequency coefficients in a classification tree/rule induction algorithm.

44. A computer-readable medium according to claim 34, wherein the polymorphic nucleic acids comprise one of DNA, RNA, tRNA, mRNA and rRNA.

* * * * *